United States Patent
Van Lierde et al.

(10) Patent No.: US 10,846,921 B2
(45) Date of Patent: Nov. 24, 2020

(54) METHOD AND SYSTEM FOR ARCHIVING SUBJECT-SPECIFIC, THREE-DIMENSIONAL INFORMATION ABOUT THE GEOMETRY OF PART OF THE BODY

(75) Inventors: Carl Van Lierde, Meerbeke (BE); Michel Janssens, Grez-Doiceau (BE)

(73) Assignees: Materialise Dental N.V., Leuven (BE); Materialise N.V., Leuven (BE)

( * ) Notice: Subject to any disclaimer, the term of this patent is extended or adjusted under 35 U.S.C. 154(b) by 0 days.

(21) Appl. No.: 13/579,372

(22) PCT Filed: Feb. 21, 2011

(86) PCT No.: PCT/EP2011/052536
§ 371 (c)(1),
(2), (4) Date: Aug. 16, 2012

(87) PCT Pub. No.: WO2011/101474
PCT Pub. Date: Aug. 25, 2011

(65) Prior Publication Data
US 2012/0317080 A1 Dec. 13, 2012

(30) Foreign Application Priority Data
Feb. 19, 2010 (GB) .................................. 1002855.3

(51) Int. Cl.
*G06F 7/00* (2006.01)
*G06T 17/00* (2006.01)
(Continued)

(52) U.S. Cl.
CPC .............. *G06T 17/00* (2013.01); *G16H 50/50* (2018.01); *G06F 19/321* (2013.01)

(58) Field of Classification Search
CPC ................................................... G06F 19/321
(Continued)

(56) References Cited

U.S. PATENT DOCUMENTS

| 9,279,602 B2* | 3/2016 | Kennedy | ................. G06Q 50/06 |
| 2004/0054653 A1* | 3/2004 | Dufourd | ................. H04N 21/63 |

(Continued)

FOREIGN PATENT DOCUMENTS

| WO | WO 2004/042660 A2 | 5/2004 |
| WO | WO 2004/042660 A3 | 5/2004 |

OTHER PUBLICATIONS

Blanz et al. "A statistical method for robust 3D surface reconstruction from sparse data," *Proceedings of the 2nd International Symposium on 3D Data Processing, Visualization, and Transmission* 293-300 (2004).

(Continued)

*Primary Examiner* — Eliyah S. Harper
(74) *Attorney, Agent, or Firm* — Clark & Elbing LLP

(57) ABSTRACT

A method and system for archiving 3D geometry information for a plurality of subjects, and on a particular part of the body (which may also be the whole body) is described. The method and system allow an organizing and an analyzing step, resulting in scalable characteristic components for the particular part of the body, and an approximation of the geometry of that particular part of the body for a specific subject by a combination of a subset of those characteristic components with corresponding scale factors, which are then stored. The method comprises the steps of: *organizing for each of said plurality of subjects the 3D geometry information according to a predetermined standard, thus obtaining organized 3D geometry information; analyzing the organized 3D geometry information of said plurality of subjects, resulting in averaged 3D geometry information of said particular part of the body; and—scalable characteristic components of said particular part of the body; such that for each of said plurality of subjects said organized 3D geometry information can be approximated by a combination of said scalable characteristic components relative to said aver- (Continued)

aged 3D geometry information; comparing, for at least one out of said plurality of subjects, said organized 3D geometry information with said averaged 3D geometry information and determining a subset of said scalable characteristic components and corresponding scale factors, for approximating to a given accuracy said organized 3D geometry information relative to said averaged 3D geometry information by a combination of said scalable characteristic components out of said subset, each characteristic component scaled with its corresponding scale factor; storing, for at least one specific subject out of said plurality of subjects, said approximated organized 3D geometry information by storing—said averaged 3D geometry information; —said subset of said scalable characteristic components and said corresponding scale factors for said specific subject.

28 Claims, 4 Drawing Sheets

(51) Int. Cl.
*G16H 50/50* (2018.01)
*G06F 19/00* (2018.01)

(58) Field of Classification Search
USPC .................... 707/999.101, 999.102, 667
See application file for complete search history.

(56) References Cited

U.S. PATENT DOCUMENTS

| | | | |
|---|---|---|---|
| 2004/0068187 A1* | 4/2004 | Krause | A61B 17/15 600/443 |
| 2005/0278156 A1 | 12/2005 | Fisher, III et al. | |
| 2006/0222209 A1* | 10/2006 | Zhang | G08B 29/188 382/107 |
| 2007/0124669 A1* | 5/2007 | Makela | G06F 16/9577 715/201 |
| 2009/0238457 A1* | 9/2009 | Rittscher | G06T 7/11 382/171 |
| 2010/0149540 A1* | 6/2010 | Boukherroub | C23C 16/401 356/445 |
| 2010/0191541 A1* | 7/2010 | Prokoski | A61B 5/0064 705/2 |
| 2019/0304568 A1* | 10/2019 | Wei | G16B 15/30 |

OTHER PUBLICATIONS

Heimann and Meinzer "Statistical shape models for 3D medical image segmentation: A review," *Medical Image Analysis* 13: 543-563 (2009).
Zheng and Schumann "3D reconstruction of a patient-specific surface model of the proximal femur from calibrated X-ray radiographs: A validation study," *Med. Phys.* 36: 1155-1166 (2009).
International Search Report and Written Opinion of the International Searching Authority for Application No. PCT/EP2011/052536 dated Aug. 4, 2011. (12 pages).
Reply to Written Opinion of the International Searching Authority for Application No. PCT/EP2011/052536 dated Dec. 5, 2011. (7 pages).
Written Opinion of the International Preliminary Examining Authority for Application No. PCT/EP2011/052536 dated Apr. 10, 2012. (7 pages).
Reply to the Written Opinion of the International Preliminary Examining Authority for Application No. PCT/EP2011/052536 dated Jun. 4, 2012. (2 pages).
International Preliminary Report on Patentability for Application No. PCT/EP2011/052536 dated Jun. 20, 2012. (9 pages).
Communication pursuant to Article 94(3) EPC for European Patent Application No. 11708752.8, dated Jul. 25, 2018 (5 pages).
Communication pursuant to Article 94(3) EPC for European Patent Application No. 11708752.8, dated Feb. 4, 2020 (4 pages).

* cited by examiner

METHOD AND SYSTEM FOR ARCHIVING SUBJECT-SPECIFIC, THREE-DIMENSIONAL INFORMATION ABOUT THE GEOMETRY OF PART OF THE BODY

CROSS-REFERENCE TO RELATED APPLICATIONS

This application is the U.S. National Stage filing under 35 U.S.C. § 371 of International Application No. PCT/EP2011/052536, filed Feb. 21, 2011, which claims the benefit of the filing date of Great Britain Patent Application No. 1002855.3, filed on Feb. 19, 2010.

BACKGROUND

The present invention relates generally to information storage and retrieval. More specifically, it relates to a system and method for the storing and archiving of information about subject-specific, three-dimensional (3D) geometry of part of the body.

A good understanding of 3D geometry of the human body is essential to many disciplines, both in the field of medicine (orthopedics, dentistry, biomedical engineering etc.) and other areas such as archaeology, physical anthropology, forensics, etc. Many techniques exist for capturing the 3D geometry (internal and external) of the human body in a direct or indirect manner e.g. CT, MRI, Ultrasound, Terahertz imaging, surface scanning, etc.

Systems for storing and retrieving 3D data have been described in the prior art (US 2005/168460, US 2008/31069). However, they all use very large datasets, and hence place high demands on storage.

SUMMARY OF THE INVENTION

An object of the present invention is to overcome the problem of having to archive large datasets of information about subject-specific, three-dimensional geometry of part of the body. The present invention reduces the amount of information to be stored per individual 3D data entry, i.e. data for a specific subject of the concerned part of the body, by taking into account characteristic components of the geometry of that concerned part of the body.

Further, 3D geometry information that is acquired by scanning contains noise and artifacts to a certain degree, dependent on the imaging equipment, the properties of the anatomical structure being scanned etc. While such noise/artifacts do not contribute to meaningful information, they do add complexity and increase the amount of data associated with the scanned body part. Moreover, the level of detail required for the 3D representation of a part of the body may vary greatly in function of the discipline/purpose for which the data is being stored/archived. As an example, one can imagine that for anthropological purposes, the characterization of a long bone such as the human femur can be limited to the overall shape (length, width, a measure for the sphericalness of the femur head, etc.), while for engineering purposes (e.g. the design of an implant) localized characteristics of the femur such as changes in the local curvature of the condyles may play a greater role and must be taken into account as well.

In embodiments of the present invention, the amount of data to be stored is reduced by eliminating irrelevant information, such as noise and/or artifacts, from the originally acquired data; moreover, the information to be stored may be limited to the degree of detail required within the context of and dictated by the purpose of use of the data, thus avoiding the storage of superfluous information.

The present invention provides a method and system for archiving 3D geometry information for a plurality of subjects, and on a particular part of the body (which may also be the whole body). The method comprises an organizing and an analyzing step, resulting in scalable characteristic components for the particular part of the body, and an approximation of the geometry of that particular part of the body for a specific subject by a combination of a subset of those characteristic components with corresponding scale factors, which are then stored. More in detail, the method comprises the steps of:

organizing for each of said plurality of subjects the 3D geometry information according to a predetermined standard, thus obtaining organized 3D geometry information;

analyzing the organized 3D geometry information of said plurality of subjects, resulting in
averaged 3D geometry information of said particular part of the body; and
scalable characteristic components of said particular part of the body; such that for each of said plurality of subjects said organized 3D geometry information can be approximated by a combination of said scalable characteristic components relative to said averaged 3D geometry information;

comparing, for at least one out of said plurality of subjects, said organized 3D geometry information with said averaged 3D geometry information and determining a subset of said scalable characteristic components and corresponding scale factors, for approximating to a given accuracy said organized 3D geometry information relative to said averaged 3D geometry information by a combination of said scalable characteristic components out of said subset, each characteristic component scaled with its corresponding scale factor;

storing, for at least one specific subject out of said plurality of subjects, said approximated organized 3D geometry information by storing
said averaged 3D geometry information;
said subset of said scalable characteristic components and said corresponding scale factors for said specific subject.

The data that is stored for a part of the body of a specific subject thus only includes a restricted number of characteristic components and their corresponding scale factors; further, averaged 3D geometry is stored for the concerned part of the body, but this does not have to be stored per subject but only once for a number of subjects. If the application requires data with less accuracy, the number of characteristic components with corresponding scale factors, and thus the storage space, can be even further restricted.

Organizing the 3D geometry according to the predetermined standard may include applying a vectorization method as discussed further below.

Analyzing the organized 3D geometry information may be done by means of covariance analysis.

The present invention also provides a system implementing the method according to the invention. The system includes a data acquisition means for acquiring the 3D data, a database component, a processor and a user interface.

The method is a computer based method. The present invention also provides a computer system, and a computer program product comprising instructions for carrying out the steps of the method according to the invention, when said computer program is executed on a computing device.

BRIEF DESCRIPTIONS OF THE DRAWINGS

DEFINITIONS

Figure 1:
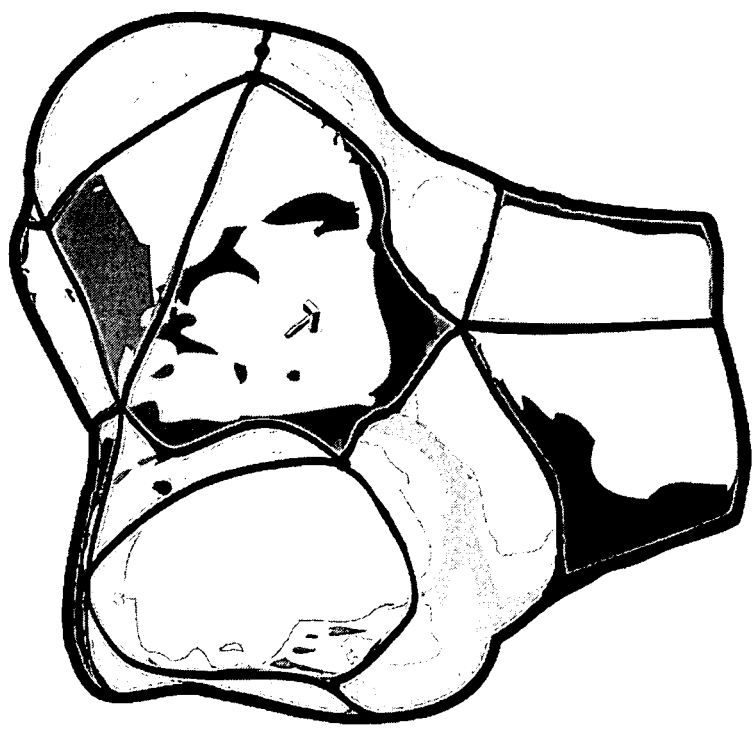
FIG. 1 shows an image of a repatched and remeshed femur image in accordance with an embodiment of the present invention.

The present invention relates to archiving shapes. A shape is a geometry and it can be 2D or 3D. The geometry can be a part of a human or animal body. Further, the geometry information also includes the outer surface of the part of the human or animal body and it may also include information about the inner structure.

The term "part of the body" may also be the whole of the body.

The term "triangulation" refers to tiling a surface of a 3D image of an object with geometrical shapes of which triangles are one example but other tiles such as polygonal tiles including three, four, five, etc. sided shapes can be used for example.

DETAILED DESCRIPTION OF THE INVENTION

The present invention will be described with respect to particular embodiments and with reference to certain drawings but the invention is not limited thereto but only by the claims. The drawings described are only schematic and are non-limiting. In the drawings, the size of some of the elements may be exaggerated and not drawn on scale for illustrative purposes. Where the term "comprising" is used in the present description and claims, it does not exclude other elements or steps. Where an indefinite or definite article is used when referring to a singular noun e.g. "a" or "an", "the", this includes a plural of that noun unless something else is specifically stated. The term "comprising", used in the claims, should not be interpreted as being restricted to the means listed thereafter; it does not exclude other elements or steps. Thus, the scope of the expression "a device comprising means A and B" should not be limited to devices consisting only of components A and B. It means that with respect to the present invention, the only relevant components of the device are A and B. Furthermore, the terms first, second, third and the like in the description and in the claims, are used for distinguishing between similar elements and not necessarily for describing a sequential or chronological order. It is to be understood that the terms so used are interchangeable under appropriate circumstances and that the embodiments of the invention described herein are capable of operation in other sequences than described or illustrated herein. Moreover, the terms top, bottom, over, under and the like in the description and the claims are used for descriptive purposes and not necessarily for describing relative positions. It is to be understood that the terms so used are interchangeable under appropriate circumstances and that the embodiments of the invention described herein are capable of operation in other orientations than described or illustrated herein.

In the drawings, like reference numerals indicate like features; and, a reference numeral appearing in more than one figure refers to the same element. The drawings and the following detailed descriptions show specific embodiments of a 3D digital endodontics system and method.

At least one method proposed in accordance with the present invention makes extensive use of statistical vector analysis and (vector-based) differential geometry. In order to use a database of shapes a one-to-one correspondence between the shapes and vectors must be established. This process is called vectorisation.

The actual analysis will be done on the set vectors so the deviations and other properties of the vectors used during the (covariance) analysis must correspond to the deviations and other properties measured on the actual shapes. Otherwise, the result of the analysis will not represent the variations in the database of shapes.

Vectorization Strategy

According to one embodiment of the current invention, 3D information of the geometry of a part of the body consists of a discrete, triangulated surface description e.g. an STL file. To obtain organized 3D information, a first step according to this embodiment is to orient the surface description with respect to a predefined (world) coordinate system. Said step can for example be performed by identifying either by means of user interaction or by means of computer automated processes (e.g. fitting Least squares, Chebychev . . . ) of a standard geometric object such as a cylinder; calculation of axes of inertia; etc.) a geometry specific coordinate system and applying a coordinate transformation to the surface description, such that the geometry specific coordinate system coincides with the predefined (world) coordinate system. A second step according to this embodiment consists of dividing the triangulated surface description into a subset of surfaces (patches) by means of a predefined approach (see FIG. 1). According to one example said approach may consist of the application of a curvature based watershed algorithm. As an alternative the division in a subset of surfaces may be the result of the application (e.g. projection) of a skeletal-framework specific for the geometry onto the surface description. Said skeletal framework has been predefined relative to said predefined (world) coordinate system and is optimized for the part of the body under consideration. It determines the boundaries of the patches and determines how the patches are subdivided in a finer grid like structure. In one example the skeletal framework determines the remeshing strategy for each patch such that the amount and distribution of triangles making up the surface description in that patch equal a certain amount and follow a certain pattern respectively (see FIG. 1).

The final step in the vectorisation is the mere concatenation of the coordinates of the different points of the remesh into one large vector. The consistency in the remesh procedure through the skeletal framework ensures a one-to-one correspondence between the shapes and the large vectors.

Analysis Method

The vectorisation allows the transformation of large database of geometries into a large database of large vectors that can be analysed using classical multi-dimensional statistical techniques, for example linear techniques, like Principal Component Analysis, but also non-linear covariance analysis techniques, like Curvilinear component analysis or advanced dimensional reduction techniques, like Sammon's linear mapping.

There are two major differences between existing methods and the method described in accordance with embodiments of the present invention:

- The skeleton explicitly does a registration of the shape being processed. This has the advantage that the analysis investigates only the variation of shape and NOT the variance in position. This gives much cleaner results on the variation in shape.
- The concatenation procedure only takes into account position differences on the shape. This implies that a covariance analysis gives meaningful results (e.g. all data is measured in the same units (mm or in) and no switch to correlation theory is required. Furthermore, adapting the local density can be used to increase the importance of certain details in the shape. No complex metric is required.

ILLUSTRATIVE EMBODIMENT

In accordance with an embodiment of the present invention a very simple vectorisation is performed for clarity purposes. The vectorisation is to be performed on a number of shapes all of which belong to the same class of shapes. The first step is to do a (re-)triangulation of the shapes to be archived. This results in a surface description such as an STL file, for example. In this embodiment triangulation is done in the same way for all examples of the shape within one class. This means that whatever shape is to be vectorised, it will have a triangulation with the same amount of triangles and that each triangle has a corresponding triangle and every point has a corresponding point in every other triangulated shape belonging to the class. The second step is to take the coordinates of each point in the (re-)triangulation and concatenate them all into one very large vector.

To make sure that the (re-)triangulation of each shape will always be topologically the same (i.e. congruent), a skeleton is used. The skeletons have only a few essential components (see FIG. 1):

- Reference points: The reference points are points that can be identified (manually or automatically) on each element of the population of one type of shape. They can have two important purposes. Firstly, they can be used for registration of each shape to a standard position. Secondly they can be used to define the topology of the (each) shape.
- Topology: The topology defines the relation between the reference points. At least, it defines how the relation should be. There are several ways to define this topology. One way is as a list of patches where the position of the patches is determined by the reference points. Another way is where the reference points are given a (typically 2D) relative position with respect to each other.
- Triangulation strategy: The goal is to have a triangulation. The skeleton defines a strict procedure to triangulate a shape following the defined topology. Applying the triangulation strategy to a shape of the population should preferably always give a congruent triangulation.

Important is that the triangulation works always, i.e. that on each shape of the population the triangulation can be performed correctly. If the triangulation strategy fails the element cannot be taken into account in the analysis. Failure can be because of a fundamental difference in topology, for example.

It is always possible to attach additional information to the skeleton (and to each shape) in order to enhance the covariance analysis.

An application that can e.g. be used with the present invention relates to archiving information defining dental casts. In orthodontics this can be a legal requirement and it can also be useful for patient follow-up.

Figure 2:
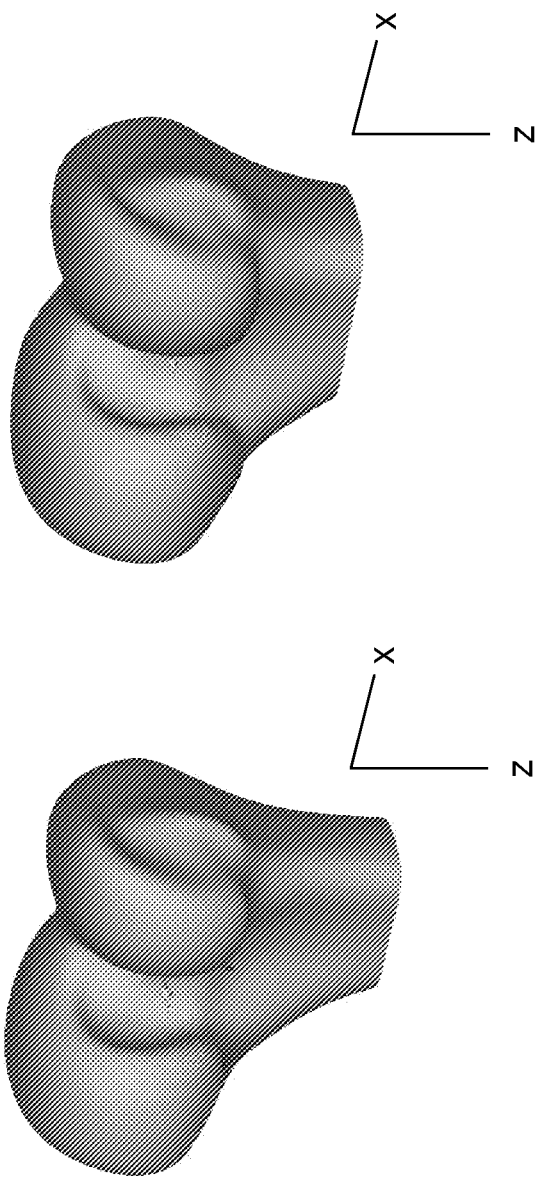
FIG. 2 shows images illustrating global parameter changing the complete shape in accordance with an embodiment of the present invention.
Figure 3:
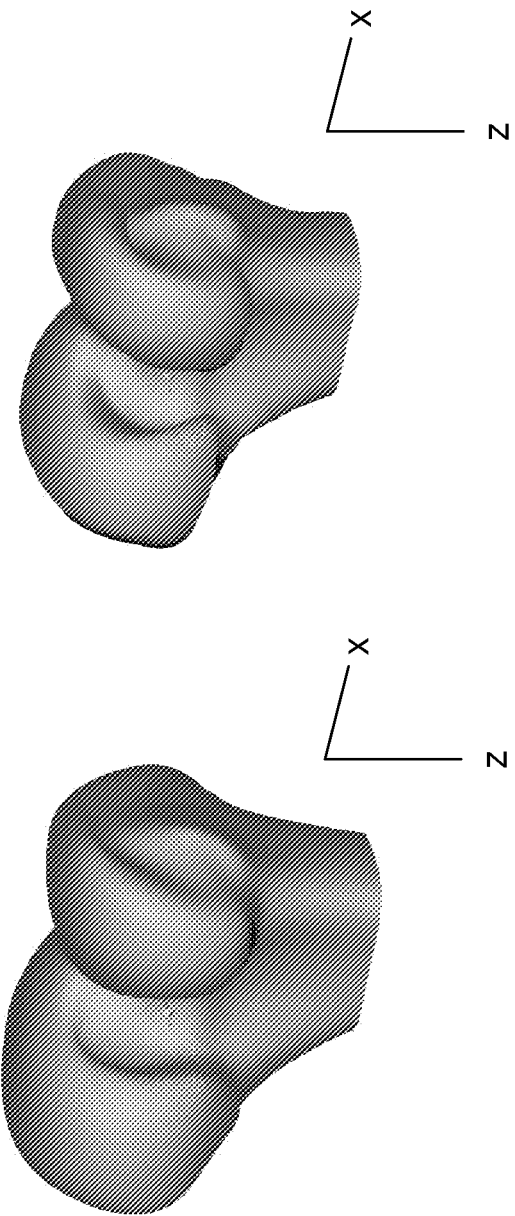
FIG. 3 shows images illustrating local parameter changing only one aspect of the geometry in accordance with an embodiment of the present invention.

In the case incomplete data need to be archived, the analysis of the organized 3D geometry will be performed only on data of the subjects for which complete data is available. The incomplete data will afterwards be compared to the average obtained via the analysis to identify the scale factors which will be stored for the subjects associated with the incomplete data. For example in one embodiment the present invention provides a method for archiving 3D geometry information for a plurality of subjects, said 3D geometry subject-specific information for a plurality of subjects being three dimensional (3D) geometry information of a particular part of the body of said subject. The method includes organizing for each of said plurality of subjects said 3D geometry information according to a predetermined standard, thus obtaining organized 3D geometry information. The standard is for example a standard or common way for all examples of the shape defining the triangulation used to provide a digital representation of the shape. The organized 3D geometry information of said plurality of subjects is analysed to obtain an averaged 3D geometry information of said particular part of the body. This means that from all the examples of one class of shape that is part of a human or animal body an average shape is determined. To define each shape scalable characteristic components of said particular part of the body are generated. This can be done by principal component analysis for example. The result is that for each of said plurality of subjects said organized 3D geometry information can be approximated by a combination of said scalable characteristic components relative to said averaged 3D geometry information. By combining at least some of the scalable characteristic components with the averaged 3D geometry information, an approximation of the original shape can be obtained. This is achieved by comparing, for at least one out of said plurality of subjects, said organized 3D geometry information with said averaged 3D geometry information and thereby determining a subset of said scalable characteristic components. FIG. 2 shows a global parameter can be used to change the complete shape. FIG. 3 shows how a local parameter can change only one aspect of the geometry. By using such changes a match can be approximated by a combination of said scalable characteristic components. For each characteristic component out said subset a scale factor is determined corresponding to said characteristic component, for approximating to a given accuracy said organized 3D geometry information relative to said averaged 3D geometry information by a combination of said scalable characteristic components out of said subset, each characteristic component scaled with its corresponding scale factor.

Then, for at least one specific subject out of said plurality of subjects, said approximated organized 3D geometry information is stored by storing the averaged 3D geometry information; the subset of said scalable characteristic components for said specific subject; and the scale factors for said specific subject and corresponding to said characteristic components out of said subset.

Organizing said 3D information according to a predetermined standard comprises defining a skeleton that can be used for each shape of a class to provide triangulation of that shape. This involves, for example, defining reference points, topology and triangulation strategy. The result is a standard triangulation for the shapes. The skeleton defines a strict procedure to triangulate a shape following the defined topology. Applying the triangulation strategy to a shape of the population should preferably always give a congruent triangulation.

Providing the 3D geometry information includes capturing said 3D geometry information using any suitable imaging equipment, e.g. selected from the group of Computerized Tomography (CT) equipment, micro CT equipment, Magnetic Resonance Imaging (MRI) equipment, optical scanning equipment and ultrasonic scanning equipment. Capturing the 3D geometry information includes capturing data directly such as from said particular part of the body or capturing data indirectly such as from an impression of said particular part of the body.

The determination of 3D geometry information of said particular part of the body is done for a plurality of subject. For these subjects the 3D geometry information is organised according to the predetermined standard, thus obtaining organized 3D geometry information for all of the subjects.

For each of the subjects the organized 3D geometry information for that subject is compared with the averaged 3D geometry information and additional subsets of said scalable characteristic components are determined. For each characteristic component out of each of the subsets a scale factor corresponding to said characteristic component is determined. This is for approximating to a given accuracy the organized 3D geometry information for said subjects relative to said averaged 3D geometry information by a combination of said scalable characteristic components out of said subsets, each characteristic component scaled with its corresponding scale factor.

Then for all of the subjects the approximated organized 3D geometry information is stored, i.e. the following is stored:
   said averaged 3D geometry information;
   the subsets of said scalable characteristic components for said other subjects;
   the scale factors for said other subjects and corresponding to said characteristic components out of said subsets.

Figure 4:
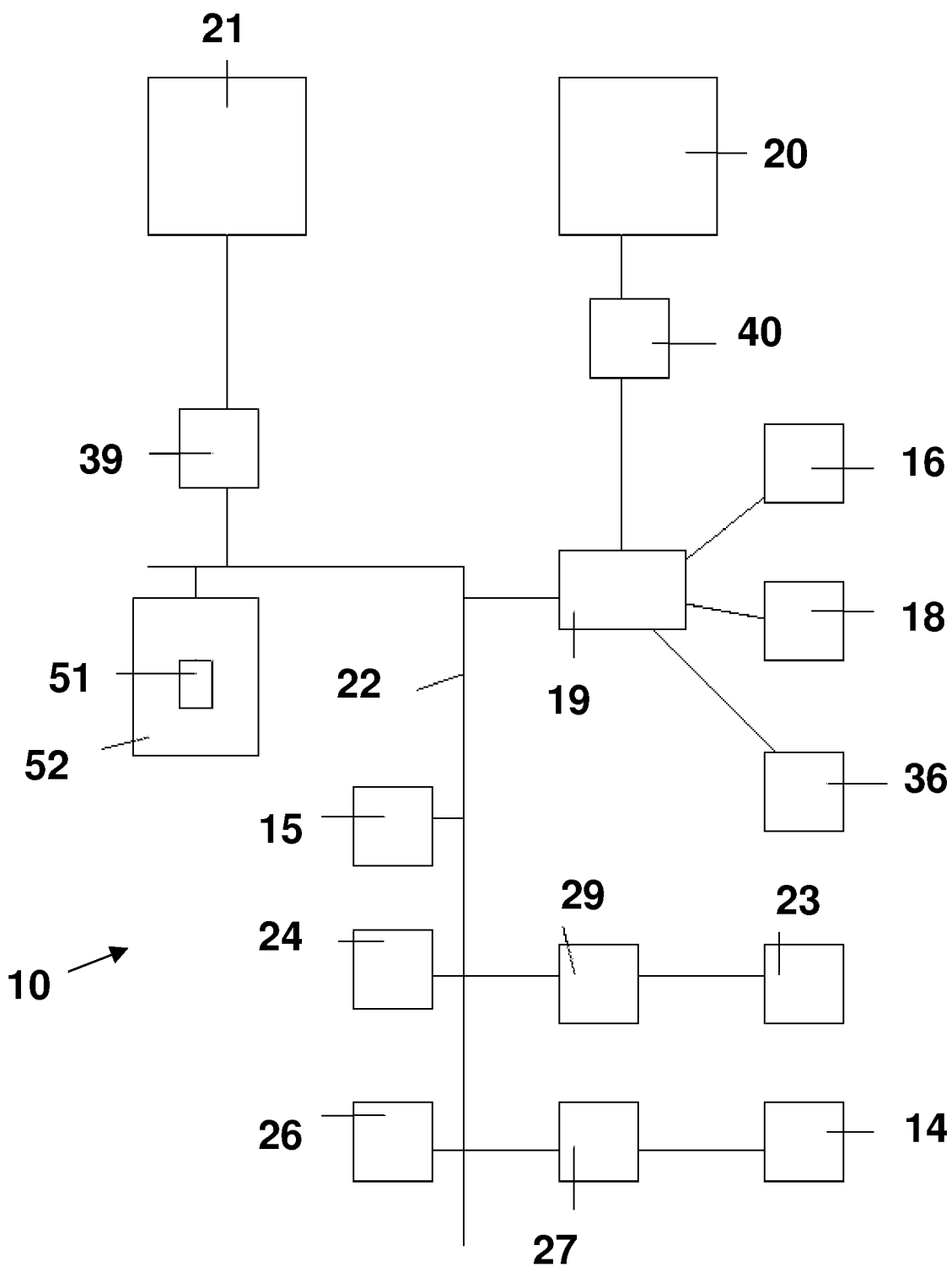
FIG. 4 is a schematic representation of a computing system which can be utilized with the methods and in a system according to embodiments of the present invention

FIG. 4 is a schematic representation of a computing system which can be utilized with the methods and in a system according to the present invention. A computer 10 is depicted which may include a video display terminal 14, a data input means such as a keyboard 16, and a graphic user interface indicating means such as a mouse 18. Computer 10 may be implemented as a general purpose computer, e.g. a UNIX workstation.

Computer 10 includes a Central Processing Unit ("CPU") 15, such as a conventional microprocessor of which a Pentium processor supplied by Intel Corp. USA is only an example, and a number of other units interconnected via system bus 22. The computer 10 includes at least one memory. Memory may include any of a variety of data storage devices known to the skilled person such as random-access memory ("RAM"), read-only memory ("ROM"), non-volatile read/write memory such as a hard disc as known to the skilled person. For example, computer 10 may further include random-access memory ("RAM") 24, read-only memory ("ROM") 26, as well as an optional display adapter 27 for connecting system bus 22 to an optional video display terminal 14, and an optional input/output (I/O) adapter 29 for connecting peripheral devices (e.g., disk and tape drives 23) to system bus 22. Video display terminal 14 can be the visual output of computer 10, which can be any suitable display device such as a CRT-based video display well-known in the art of computer hardware. However, with a portable or notebook-based computer, video display terminal 14 can be replaced with a LCD-based or a gas plasma-based flat-panel display. Computer 10 further includes user interface adapter 19 for connecting a keyboard 16, mouse 18, optional speaker 36, as well as allowing optional image data to be input from image capture devices such as imaging devices 40 of an external imaging system 20. The devices 40 may be any suitable imaging devices for capturing an image of a object such as a part of the body. These devices may include MRI, CT-scan, optical, X-ray, PET-scan devices or similar devices. An archiving system 21 may also connected to bus 22 via a communication adapter 39 connecting computer 10 to a data network such as the Internet, an Intranet a Local or Wide Area network (LAN or WAN) or a CAN. This allows remote storing of the 3D results of the present invention, i.e. the following can be stored:
   averaged 3D geometry information;
   the subsets of said scalable characteristic components for said other subjects;
   the scale factors for said other subjects and corresponding to said characteristic components out of said subsets.

Alternatively this information may be stored locally to computer 10 in a suitable digital storage device. Inputs to computer 10 such as images of an object such as a part of the body may be input directly into the computer using storage devices such as 23.

Computer 10 also includes a graphical user interface that resides within machine-readable media to direct the operation of computer 10. Any suitable machine-readable media may retain the graphical user interface, such as a random access memory (RAM) 24, a read-only memory (ROM) 26, a magnetic diskette, magnetic tape, or optical disk (the last three being located in disk and tape drives 23). Any suitable operating system and associated graphical user interface (e.g., Microsoft Windows) may direct CPU 15. In addition, computer 10 includes a control program 51 which resides within computer memory storage 52. Control program 51 contains instructions that when executed on CPU 15 carry out the operations described with respect to any of the methods of the present invention.

The computer system of FIG. 4 including a computer 10 and optional network components is adapted, i.e. has software running on the computer in co-operation with the processor for archiving 3D geometry information for a plurality of subjects, said 3D geometry information for a plurality of subjects subject-specific being three dimensional (3D) geometry information of a particular part of the body of said subject.

The computer system is adapted, i.e. has software running on the computer in co-operation with the processor for organizing for each of said plurality of subjects said 3D geometry information according to a predetermined standard, thus obtaining organized 3D geometry information.

The computer system is adapted, i.e. has software running on the computer in co-operation with the processor for analyzing said organized 3D geometry information of said plurality of subjects resulting in
   averaged 3D geometry information of said particular part of the body; and
   scalable characteristic components of said particular part of the body;

such that for each of said plurality of subjects said organized 3D geometry information can be approximated by a combination of said scalable characteristic components relative to said averaged 3D geometry information.

The computer system is adapted, i.e. has software running on the computer in co-operation with the processor for comparing, for at least one out of said plurality of subjects, said organized 3D geometry information with said averaged 3D geometry information and determining a subset of said scalable characteristic components and for each characteristic component out said subset a scale factor corresponding to said characteristic component, for approximating to a given accuracy said organized 3D geometry information relative to said averaged 3D geometry information by a combination of said scalable characteristic components out of said subset, each characteristic component scaled with its corresponding scale factor.

The computer system is adapted, i.e. has software running on the computer in co-operation with the processor for storing, either locally or remotely, for at least one specific subject out of said plurality of subjects, said approximated organized 3D geometry information by storing
said averaged 3D geometry information;
said subset of said scalable characteristic components for said specific subject;
said scale factors for said specific subject and corresponding to said characteristic components out of said subset.

The computer system is preferably adapted, i.e. has software running on the computer in co-operation with the processor for organizing said 3D information according to a predetermined standard comprises vectorization.

The computer system is preferably adapted, i.e. has software running on the computer in co-operation with the processor for providing said 3D geometry information by capturing said 3D geometry information using imaging equipment such as equipment 40 in imaging system 20. The imaging equipment 40 can be selected from the group of Computerized Tomography (CT) equipment, micro CT equipment, Magnetic Resonance Imaging (MRI) equipment, optical scanning equipment and ultrasonic equipment.

The computer system is preferably adapted, i.e. has software running on the computer in co-operation with the processor for capturing said 3D geometry information by capturing data directly such as from said particular part of the body.

The computer system is preferably adapted, i.e. has software running on the computer in co-operation with the processor for capturing said 3D geometry information by capturing data indirectly such as from an impression of said particular part of the body.

The computer system is preferably adapted, i.e. has software running on the computer in co-operation with the processor, for:
providing said 3D geometry information of said particular part of the body for another subject;
organizing said 3D geometry information for said other subject according to said predetermined standard, thus obtaining organized 3D geometry information for said other subject;
comparing said organized 3D geometry information for said other subject with said averaged 3D geometry information and determining another subset of said scalable characteristic components and for each characteristic component out said other subset a scale factor corresponding to said characteristic component, for approximating to a given accuracy said organized 3D geometry information for said other subject relative to said averaged 3D geometry information by a combination of said scalable characteristic components out of said other subset, each characteristic component scaled with its corresponding scale factor;
storing for said other subject said approximated organized 3D geometry information by storing
said averaged 3D geometry information;
said subset of said scalable characteristic components for said other subject;
said scale factors for said other subject and corresponding to said characteristic components out of said subset.

Those skilled in the art will appreciate that the hardware represented in FIG. 4 may vary for specific applications. For example, other peripheral devices such as optical disk media, audio adapters, or chip programming devices, such as PAL or EPROM programming devices well-known in the art of computer hardware, and the like may be utilized in addition to or in place of the hardware already described.

In the example depicted in FIG. 4, the computer program product (i.e. control program 51) can reside in computer storage 52. However, it is important that while the present invention has been, and will continue to be, that those skilled in the art will appreciate that the mechanisms of the present invention are capable of being distributed as a program product in a variety of forms, and that the present invention applies equally regardless of the particular type of signal bearing media used to actually carry out the distribution. Examples of computer readable signal bearing media include: recordable type media such as floppy disks and CD ROMs and transmission type media such as digital and analogue communication links.

The invention claimed is:

1. A computer based method for archiving three-dimensional (3D) geometry information for at least one specific subject from a plurality of subjects as an approximated organized 3D geometry information, said 3D geometry information for at least one specific subject from a plurality of subjects being subject-specific 3D geometry information of a particular part of the body,
the method comprising, in cooperation with at least one processor and at least one storage device, the steps of:
(a) organizing for said plurality of subjects said 3D geometry information according to a predetermined standard, thus obtaining organized 3D geometry information;
(b) analyzing said organized 3D geometry information resulting in
(i) averaged 3D geometry information of said particular part of the body, wherein said averaged 3D geometry information comprises the average shape of said particular part of the body of said plurality of subjects; and
(ii) scalable characteristic components of said particular part of the body;
such that for each of said plurality of subjects said organized 3D geometry information is capable of being approximated by a combination of said scalable characteristic components relative to said averaged 3D geometry information;
(c) comparing, for said specific subject, said organized 3D geometry information for said specific subject with said averaged 3D geometry information to determine (i) a subset of said scalable characteristic components and (ii) for each characteristic component from said subset, a scale factor corresponding to said characteristic component for approximating to a given accuracy said organized 3D geometry information for said specific subject relative to said averaged 3D geometry information by a combination of said scalable characteristic components out of said subset, each characteristic component scaled with its corresponding scale factor; and (d) storing, for said specific subject, said approximated organized 3D geometry information by storing
said averaged 3D geometry information;
said subset of said scalable characteristic components for said specific subject; and
for each characteristic component from said subset, said scale factor for said specific subject;
thereby archiving 3D geometry information for said specific subject.

2. The method according to claim 1 wherein said organizing said 3D information according to a predetermined standard comprises vectorization.

3. The method according to claim 1, wherein said method further comprises providing said 3D geometry information, said providing said 3D geometry information comprising capturing said 3D geometry information using imaging equipment.

4. The method according to claim 3, wherein said imaging equipment is selected from the group consisting of Computerized Tomography (CT) equipment, micro CT equipment, Magnetic Resonance Imaging (MRI) equipment, optical scanning equipment, and ultrasonic equipment.

5. The method according to claim 3, wherein said capturing said 3D geometry information comprises capturing data directly such as from said particular part of the body.

6. The method according to claim 3, wherein said capturing said 3D geometry information comprises capturing data indirectly from an impression of said particular part of the body.

7. The method according to claim 1, further comprising the steps of:
providing 3D geometry information of said particular part of the body for another subject;
organizing said 3D geometry information for said another subject according to said predetermined standard, thus obtaining organized 3D geometry information for said another subject;
comparing said organized 3D geometry information for said another subject with said averaged 3D geometry information to determine (i) another subset of said scalable characteristic components and (ii) for each characteristic component from said other subset, a scale factor corresponding to said characteristic component for approximating to a given accuracy said organized 3D geometry information for said another subject relative to said averaged 3D geometry information by a combination of said scalable characteristic components out of said another subset, each characteristic component scaled with its corresponding scale factor; and
storing, for said another subject, said approximated organized 3D geometry information by storing
said averaged 3D geometry information;
said subset of said scalable characteristic components for said another subject; and
for each characteristic component from said another subset, said scale factor for said another subject;
thereby archiving 3D geometry information for said another subject.

8. A non-transitory computer readable storage medium comprising instructions for carrying out the steps of the method according to claim 1, when said non-transitory computer readable storage medium is executed.

9. A machine readable recording device on which is stored the non-transitory computer readable storage medium of claim 8.

10. A computer system for archiving 3D geometry information for at least one specific subject from a plurality of subjects as an approximated organized 3D geometry information, said 3D geometry information for at least one specific subject from a plurality of subjects being subject-specific 3D geometry information of a particular part of the body, the system, in cooperation with at least one processor and at least one storage device, comprising:

(a) means for organizing for said plurality of subjects said 3D geometry information according to a predetermined standard, thus obtaining organized 3D geometry information;

(b) means for analyzing said organized 3D geometry information resulting in
(i) averaged 3D geometry information of said particular part of the body, wherein said averaged 3D geometry information comprises the average shape of said particular part of the body of said plurality of subjects; and
(ii) scalable characteristic components of said particular part of the body;
such that for each of said plurality of subjects said organized 3D geometry information is capable of being approximated by a combination of said scalable characteristic components relative to said averaged 3D geometry information;

(c) means for comparing, for said specific subject, said organized 3D geometry information for said specific subject with said averaged 3D information to determine (i) a subset of said scalable characteristic components and (ii) for each characteristic component from said subset, a scale factor corresponding to said characteristic component for approximating to a given accuracy said organized 3D geometry information for said specific subject relative to said averaged 3D geometry information by a combination of said scalable characteristic components out of said subset, each characteristic component scaled with its corresponding scale factor; and (d) means for storing, for said specific subject, said approximated organized 3D geometry information by storing
said averaged 3D geometry information;
said subset of said scalable characteristic components for said specific subject; and
for each characteristic component from said subset, said scale factor for said specific subject;
thereby archiving 3D geometry information for said specific subject.

11. The system according to claim 10, wherein said means for organizing said 3D information according to a predetermined standard comprises means for vectorization.

12. The system according to claim 10, wherein system further comprises means for providing said 3D geometry information, said means for providing said 3D geometry information comprising means for capturing said 3D geometry information using imaging equipment.

13. The system according to claim 12, wherein said imaging equipment is selected from the group consisting of Computerized Tomography (CT) equipment, micro CT equipment, Magnetic Resonance Imaging (MRI) equipment, optical scanning equipment, and ultrasonic equipment.

14. The system according to claim 12, wherein said means for capturing said 3D geometry information comprises means for capturing data directly from said particular part of the body.

15. The system according to claim 12, wherein said means for capturing said 3D geometry information comprises means for capturing data indirectly such as from an impression of said particular part of the body.

16. The system according to claim 10 further comprising:
means for providing 3D geometry information of said particular part of the body for another subject;
means for organizing said 3D geometry information for said another subject according to said predetermined standard, thus obtaining organized 3D geometry information for said another subject;
means for comparing said organized 3D geometry information for said other subject with said averaged 3D geometry information to determine (i) another subset of said scalable characteristic components and (ii) for each characteristic component from said another subset, a scale factor corresponding to said characteristic component for approximating to a given accuracy said organized 3D geometry information for said another subject relative to said averaged 3D geometry information by a combination of said scalable characteristic components out of said another subset, each characteristic component scaled with its corresponding scale factor; and
means for storing, for said another subject, said approximated organized 3D geometry information by storing said averaged 3D geometry information;
said subset of said scalable characteristic components for said another subject; and
for each characteristic component from said another subset, said scale factor for said another subject; thereby archiving 3D geometry information for said another subject.

17. The method according to claim 1, wherein said method reduces 3D geometry information for said particular part of the body.

18. The system according to claim 10, wherein said system reduces said 3D geometry information for said particular part of the body.

19. The method according to claim 2, wherein said 3D geometry information is a triangulated surface.

20. The method according to claim 19, wherein the step of organizing comprises the step of orienting said triangulated surface according to a predefined coordinate system.

21. The method of claim 20, wherein said method is an automated process.

22. The method of claim 19, wherein the step of organizing comprises the step of dividing said triangulated surface into a subset of surfaces.

23. The method of claim 22, wherein said subset of surfaces is divided by applying a skeletal framework.

24. The system according to claim 11, wherein said 3D geometry information is a triangulated surface.

25. The system according to claim 24, wherein said means for organizing comprises orienting said triangulated surface according to a predefined coordinate system.

26. The system of claim 25, wherein said system is automated.

27. The system of claim 24, wherein said means for organizing comprises dividing said triangulated surface into a subset of surfaces.

28. The system of claim 27, wherein said subset of surfaces is divided by applying a skeletal framework.

* * * * *